United States Patent [19]
Fogarty et al.

[11] Patent Number: 5,514,151
[45] Date of Patent: May 7, 1996

[54] VALVULOTOME WITH A LATERALLY OFFSET CURVED CUTTING EDGE

[76] Inventors: Thomas J. Fogarty, 5660 Alpine Rd., Portola Valley, Calif. 94028; Thomas A. Howell, 567 Homer, Palo Alto, Calif. 94301

[21] Appl. No.: 301,324

[22] Filed: Sep. 6, 1994

Related U.S. Application Data

[63] Continuation of Ser. No. 985,131, Dec. 2, 1992, abandoned.

[51] Int. Cl.$^6$ .................................................. A61B 17/32
[52] U.S. Cl. ............................................ 606/159; 606/170
[58] Field of Search ............................ 606/1, 106, 108, 606/110, 113, 159, 167, 170; 604/22, 26, 27, 35, 164, 264, 268, 272

[56] References Cited

U.S. PATENT DOCUMENTS

| | | | |
|---|---|---|---|
| 2,676,595 | 4/1954 | Dyekjaer | 606/159 |
| 4,768,508 | 9/1988 | Chin et al. | |
| 4,952,215 | 8/1990 | Ouriel et al. | 606/159 |
| 5,026,383 | 6/1991 | Nobles | 606/159 |
| 5,069,679 | 12/1991 | Taheri | 606/159 |
| 5,087,264 | 2/1992 | Miller et al. | 606/159 |
| 5,092,872 | 3/1992 | Segalowitz | 606/170 |
| 5,133,725 | 6/1992 | Quadri | 606/159 |
| 5,141,491 | 8/1992 | Bowald | 606/159 |
| 5,152,771 | 10/1992 | Sabbaghian et al. | 606/159 |
| 5,171,316 | 12/1992 | Mehigan | 606/159 |

FOREIGN PATENT DOCUMENTS

| | | | |
|---|---|---|---|
| 3942589 | 7/1991 | Germany | 606/170 |
| 8906936 | 8/1989 | WIPO | 606/167 |

OTHER PUBLICATIONS

Valvulomtonmy of Valves in the Saphenous Vein Graft Before Coronary Artery Bypass Mills et al–pp. 878–879–Biosurge vol. 71 Nov. 6 Jun. 1976–Feb. 23, 1988.
"The New Hall Valvulotome," product leaflet published by Solco Basle, Inc., copyright date: 1990.
"Insitucat Valvulotome," product leaflet published by Aesculap, date unknown.
"Leather Retrograde Valvulotome," product leaflet published by Baxter International, Inc. Copyright date, 1990.
"The Olympus Valvulotomes," product leaflet published by Olympus Corporation, Copyright date: 1990.
"The LeMaitre Valvulotome System," product leaflet published by Vascutech, Inc., date unknown.
"Leather Karmody In Situ Bypass Set," product leaflet published by American Hospital Supply Corporation, copyright date: 1964.
Baxter Healthcare Corporation Catalog, pp. E115 and E116 showing three types of Leather brand valvulotomes; copyright date: 1988.
Pilling catalog, p. 226, showing Mills Valvulotome, Coarctation hook, and other, unnumbered pages showing DeBakey valve hooks, and other microsurgery instruments; date unknown.

Primary Examiner—Stephen C. Pellegrino
Assistant Examiner—Glenn Dawson
Attorney, Agent, or Firm—Limbach & Limbach; Raymond Sun

[57] ABSTRACT

A valvulotome that cuts a vein valve leaflet from apex to edge by applying a tensile force to the leaflet. The valvulotome has a shaft, on the distal end of which is a laterally-offset extension, to the distal end of which is attached the distal end of a blade with a curved cutting edge. The blade is substantially parallel to the shaft. The cutting edge faces the extension, which shields the cutting edge. Opposite the cutting edge, the blade has a blunt back that has a substantially straight part, and a part, towards its proximal end, that curves towards the extension. The blade may be pivotally attached to the extension with an actuator that opens or closes the blade. A method of using the valvulotome to carry out a valvotomy in a vein includes piercing the valve leaflet with the valvulotome close to the apex of the leaflet, and applying a tensile force to the leaflet with the valvulotome to cut the leaflet from apex to edge.

10 Claims, 6 Drawing Sheets

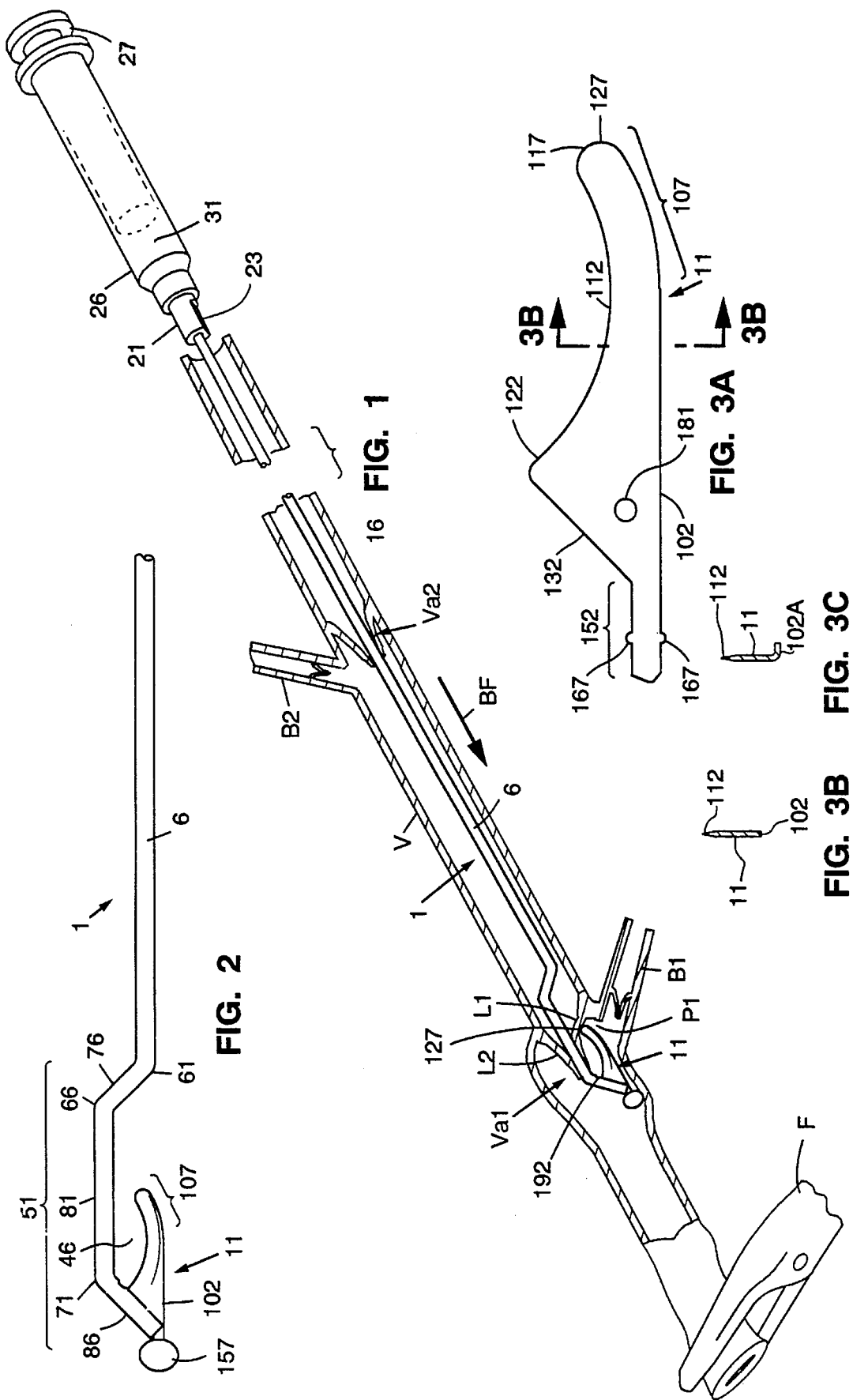

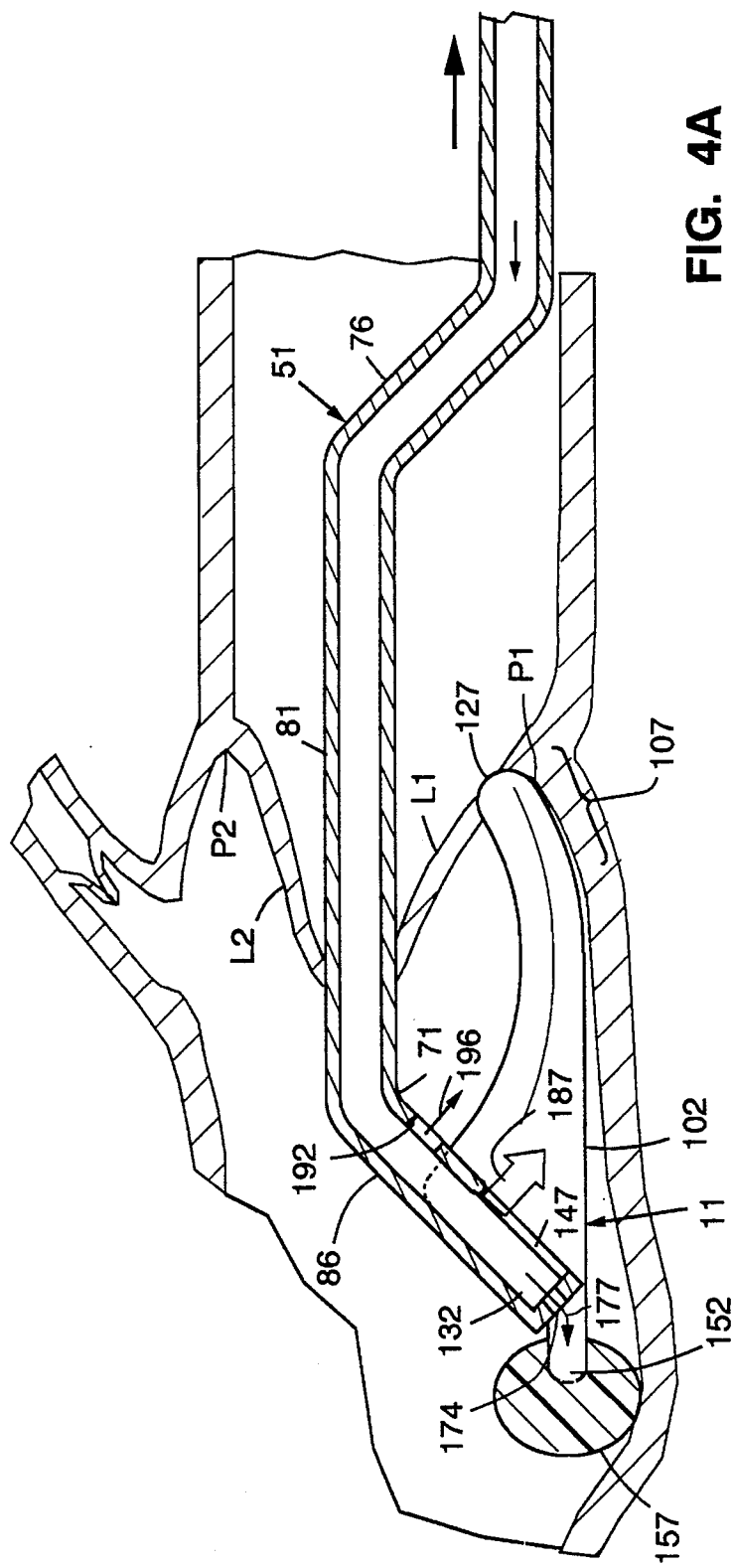
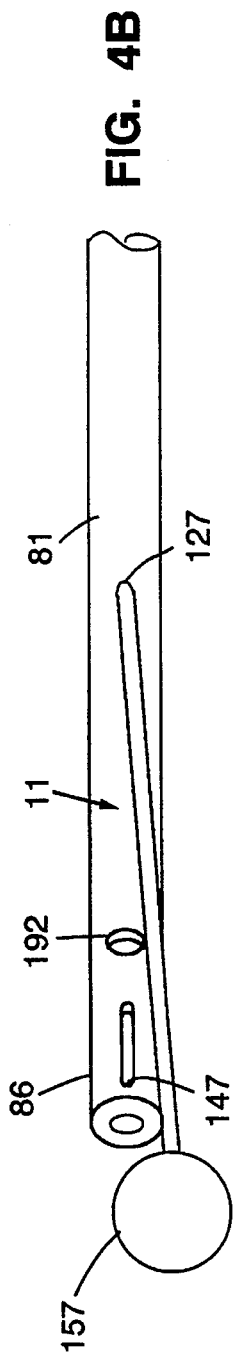
FIG. 4A
FIG. 4B

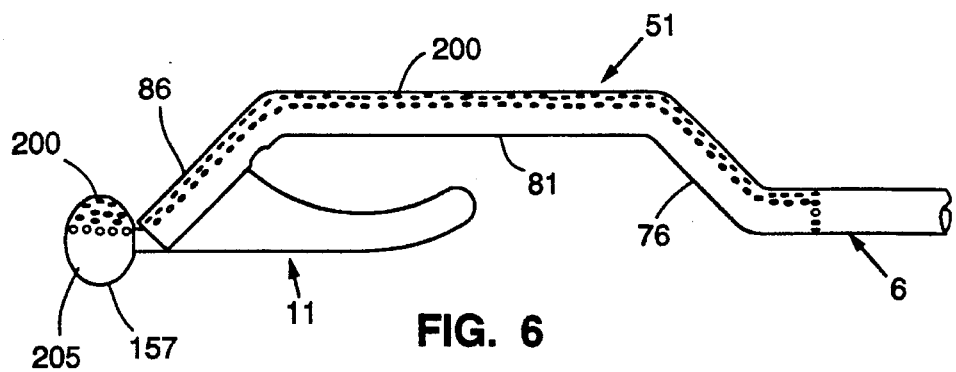
FIG. 6
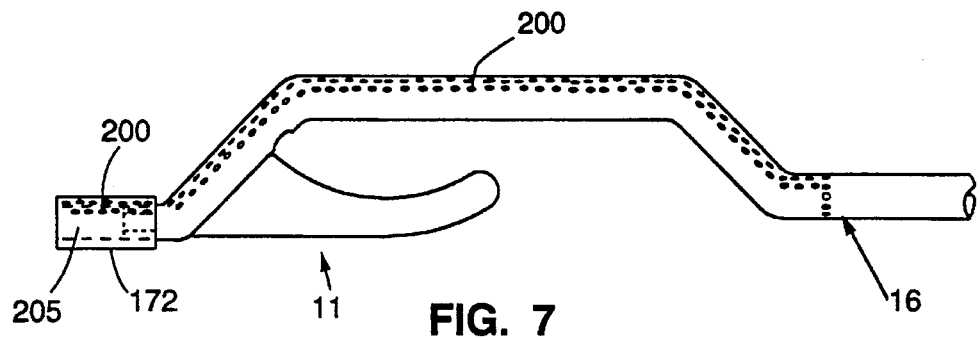
FIG. 7
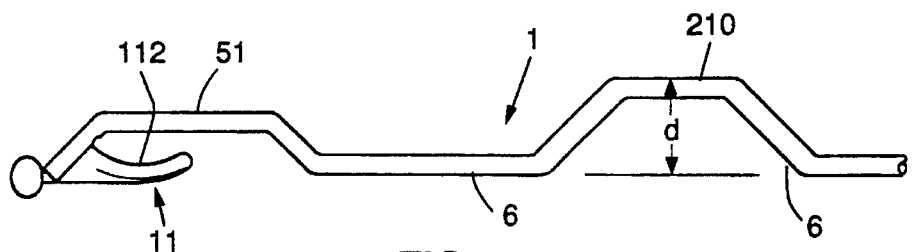
FIG. 8
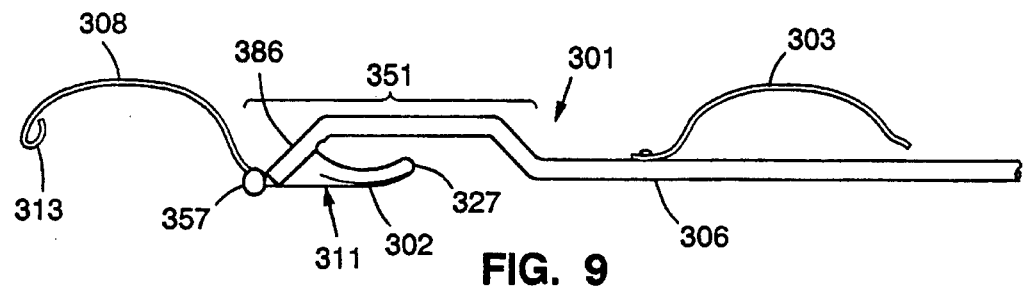
FIG. 9
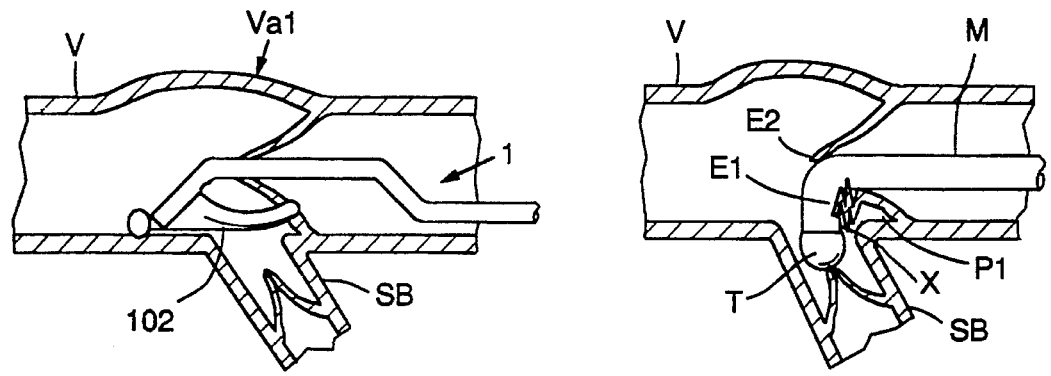
FIG. 10
(PRIOR ART)
FIG. 11

5,514,151

VALVULOTOME WITH A LATERALLY OFFSET CURVED CUTTING EDGE

This is a continuation of application Ser. No. 07/985,131 filed on 2 Dec. 1992, now abandoned.

BACKGROUND OF THE INVENTION

The present invention relates to a vein valve cutter (also called a valvulotome) for use in disrupting vein valves during vascular reconstructive surgery. This invention relates to apparatus to disrupt venous valves in vein segments used in the Coronary Artery Bypass Graft (CABG) procedure, and also for use in the In Situ Bypass procedure, and methods of using the apparatus in such procedures.

In the CABG procedure, occlusive disease in the coronary arteries is routinely bypassed with segments of saphenous vein removed from the leg. It is advantageous to place the saphenous vein used as the bypass conduit in the non-reversed orientation. For the saphenous vein to be used in the non-reversed orientation, the valves of the vein must be rendered incompetent. Even if the saphenous vein is used in the reversed orientation, the valves of the vein must be rendered incompetent, since competent valve leaflets can be a site for future clot formation behind the leaflet, which can compromise the viability of the graft.

In the In Situ bypass procedure, occlusive disease in the arterial system of the leg is bypassed with a segment of adjacent saphenous vein left undissected from the surrounding tissue. For blood to flow in its new direction, the valves in the saphenous vein segment must be obliterated. In this procedure, it is often desirable to view the valve-cutting process directly using a fiber optic scope inserted into the vein.

In both the CABG and the In Situ procedures, an infusion of physiologic solution into the vein is useful to identify the valve by clearing the field of view and temporarily closing the valves.

Previous efforts to disrupt the valves within a vein have led to a number of devices and techniques.

One form of valvulotome, called a Mills valvulotome, consists of a long, thin shaft with a short, narrow blade at its distal end. The blade is approximately perpendicular to the longitudinal axis of the shaft. The end of the blade remote from the shaft has a small spherical tip. The blade has a cutting edge along substantially all of its proximal edge, while the distal edge is dull.

A significant shortcoming of the L-shaped design of the Mills valvulotome is the propensity for the blade to snag on side branches of the saphenous vein. This tendency is both cumbersome for the surgeon and also can compromise the integrity of the vein graft. The blade of the Mills valvulotome is small enough to enter side branches easily and, once engaged within the branch, can cut the wall of the vein.

Another type of valvulotome design consists of a wire with a large bullet-shaped tip and round guide pulled by a catheter. The cutting element is located at the proximal end of the bullet tip. Valvulotomes of this design include the LeMaitre, Leather, Hall and Insitucat styles. This design is less prone to catching in side branches but has the disadvantages of being bulky, incompatible with angioscopy for visualization of the cutting-process, and is effective only over a narrow range of vein diameters. Also, the Leather, Hall and Insitucat designs require proper rotational orientation to align properly with the valve cusps, a requirement that is difficult to achieve, given their incompatibility with fiber optic viewing. Moreover, devices of this design tend to tear the valve instead of cut it because the cutting force is simultaneously applied to a relatively large area of the valve.

In another valvulotome design, the valve is cut by a plurality of blunt fingers extending from the end of a catheter. The cutter fingers are shielded except when exposed by the user to engage the valve. A fiber optic viewer extends up the center bore of the catheter to directly observe the cutting process. In this design, the fiber optics are an integral part of the valvulotome. This design, with its many moving parts, has the disadvantage of being difficult to manufacture. Moreover, the fingers' bluntness, as well as their plurality, tend to rip the valve in a random manner, leaving the vein wall in an unpredictable condition.

OBJECTS AND SUMMARY OF THE INVENTION

Therefore, it is an object of the present invention to produce a valvulotome that simplifies the operation of disrupting the valves in a vein; reduces the tendency to snag a sidebranch, yet easily engages and aligns with the valves to be cut; and truly cuts the valve neatly. It is also an object of the present invention to provide a valvulotome that provides fluid irrigation; can be used either with, or without direct visualization; and is inherently simple to manufacture.

A valvulotome according to the invention has a shaft with a laterally offset extension on its distal end. The distal end of a short blade with one cutting edge is attached to the distal end of the extension. The blade is substantially parallel to the shaft and its cutting edge faces the extension which shields the cutting edge of the blade. The cutting edge of the blade is preferably concavely curved. The back of the blade, opposite the cutting edge, is blunt. The blunt side of the blade is substantially straight over part of its length, but, towards its proximal end, curves inward towards the extension.

In the preferred embodiment, the curvature of the back of the blade substantially follows the curvature of the cutting edge. Both ends of the blade are blunt. At least part of the distal end is adapted for attaching the blade to the extension. The proximal end of the blade stops short of the distal end of the shaft, providing a gap between the blade and the extension into which the leaflet of the valve can pass for cutting. Viewed from the side, the valvulotome appears like a deep hook.

The distal end of the valvulotome is provided with either a rigid substantially spheroidal tip, or a tubular flexible tip. The tip is preferably provided with two colors to enable the orientation of the valvulotome to be observed through the translucent wall of the vein. The tip is colored so that when the valvulotome is observed from the edge and is oriented with its blade facing towards the observer, only the first color of the tip can be seen. When the valvulotome is oriented with its blade facing away from the observer, only the second color of the tip can be seen. It is also desirable that part of the extension remote from the blade be colored with a dark color to contrast with the shiny gold colored blade to further aid external observation of the valvulotome.

The shaft and extension of the valvulotome according to the invention are preferably hollow. Physiologic solution pumped through the shaft and the extension passes out of one or more holes in the wall of the extension in the vicinity of the blade attachment point of the blade. The physiologic solution provides inflation that aids in locating the valves in the vein and also holds at least one of the leaflets in place while it is being cut. Holes may be provided to allow physiologic solution to spray out of the tip of the valvulotome, or to spray in a fan pattern or in a jet pattern out of the extension of the valvulotome towards the blade. Finally, a hole may be provided to allow physiologic solution to flow in a laminar manner over the blade.

In an alternative embodiment of a valvulotome according to the invention, the blade is pivotally attached to the extension. An actuating device controls the blade's movement between an open position and a closed position. In the closed position, the valvulotome has a low profile, and the extension completely covers the cutting edge of the blade. In the open position, the blade is correctly positioned for cutting valves.

In a first variation, the blade is unbiased. Contact between the back of the blade and the vein wall moves the blade to its closed position. The actuating device is a jet of physiologic solution impinging on the blade that moves the blade to its open position. In a second variation, a spring biases the blade towards the closed position, and the actuating device is a cable that pulls the blade towards the open position. In a third variation, a spring biases the blade towards its closed position and the actuating device is a jet of physiologic solution impinging on the blade that moves the blade towards the open position. In a fourth variation, a spring biases the blade towards its open position, and the actuating device is a cable that pulls the blade towards the closed position.

The valvulotome according to the invention is intended to be used by one surgeon without an assistant. The proximal end of the shaft of the valvulotome is attached to a syringe. The surgeon holds the vein with one hand and manipulates the valvulotome assembly, comprising the valvulotome and the syringe, with the other. The surgeon inserts the valvulotome into the vein and advances the valvulotome up the vein in the normal direction, i.e., the direction of normal blood flow.

The valvulotome presents to the wall of the vein three relatively large, blunt surfaces: to one side, the tip of the valvulotome and the back of the blade; and, to the other side, the back of the extension. The dimensions of the surfaces that the valvulotome presents to the wall of the vein are larger than the diameter of the entries of side branches of the vein, which makes the valvulotome automatically reject entry into such side branches. Moreover, the broad, blunt surfaces of the valvulotome significantly reduce the possibility of the valvulotome penetrating the wall of the vein compared with known valvulotomes. Finally, the cutting edge of the blade of the valvulotome is shielded by the extension. Therefore, the valvulotome may be allowed to make contact with the walls of the vein since there is minimal risk of the valvulotome damaging the vein. This allows the valvulotome to be self guiding as it is advanced up the vein, and enables the surgeon to use the valvulotome without internal observation.

The position of the valvulotome in the vein can be determined from outside the vein by observing the imprint of the shape of the extension and the shape of the tip on the wall of the vein. The rotational orientation of the valvulotome relative to its longitudinal axis can be judged by observing the colored tip and extension of the valvulotome through the translucent wall of the vein, and also by observing or feeling the position of a thumb bump on the luer fitting connecting the shaft to the syringe.

The surgeon passes the valvulotome through the vein in the normal direction past all the valves in the vein, until the blade passes the last valve in the vein. The surgeon then withdraws the valvulotome slowly until the proximal end of the blade encounters the last valve. While the valvulotome is being withdrawn, the surgeon infuses solution using the syringe. The solution emerges from the holes in the valvulotome and causes the valve to close. When the blade encounters the closed valve, it automatically locates the valvulotome into the optimum position to cut the leaflet, which enables the leaflet to be cut without internal observation. The proximal end of the blade contacts the leaflet and slides down the plane of the leaflet until it encounters the apex of the leaflet in the base of the valve pocket, i.e., at the junction between the leaflet and the wall of the vein. Pulling the proximal end of the blade into the valve pocket orientates the valvulotome rotationally so that the plane of the blade is perpendicular to the edge of the leaflet, and locates the blade laterally so that the blade will cut the leaflet in its center.

Once in the valve pocket, the proximal end of the blade cannot slide further, and further withdrawal of the valvulotome causes the proximal end of the blade to pierce the leaflet. The blade is then hooked through the leaflet, and the only way that the blade can disengage itself from the leaflet is to cut the leaflet all the way to the edge. When cutting the leaflet, the blade applies a tensile force to the leaflet rather than a compressive force. The leaflet is relatively strong in tension and so can provide the resistance necessary for the blade to cut it cleanly.

After the first leaflet has been cut, the surgeon advances the valvulotome back up the vein once more, rotates it through approximately 180 degrees, and cuts the second leaflet using the same procedure as described above. The valvulotome is then withdrawn down the vein and the cutting process is repeated to cut all the other valves in the vein.

In the preferred embodiment of the valvulotome according to the invention, the shaft and extension of the valvulotome are hollow. In the preferred method according to the invention of using the preferred embodiment of the invention, a syringe is attached to the proximal end of the shaft. The preferred method is similar to the method just described, but when the valvulotome has been advanced past the last valve in the vein, the surgeon clamps the end of the vein downstream (in the normal direction) of the last valve with a vascular occlusive clip. The surgeon operates the syringe with the other hand to infuse physiologic solution from the syringe through the shaft and the extension to exit from the extension in the vicinity of the blade. The solution inflates the vein between the clamp and the last valve and enables the location of the valve to be determined. The pressure caused by the solution closes the valve, forcing the edge of each leaflet into contact with the shaft of the valvulotome. This ensures that the edges of the leaflets are in the center of the vein and that, when the valvulotome is withdrawn, its blade engages with a leaflet. The preferred embodiment of the valvulotome has a blade that is curved to match the curve of the inflated vein wall. This enables the end of the blade to locate the apex of the leaflet in the base of the valve pocket more accurately.

Cutting the first leaflet releases some pressure above the valve, but the solution may not drain away immediately and the surgeon may be able to advance the valvulotome and rotate it quickly enough to cut the second leaflet while there is still some pressure behind it. This cannot be relied upon, however, since the purpose of cutting the leaflets is to destroy their ability to resist the passage of a fluid. Thus, in the preferred method according to the invention of using the preferred embodiment of a valvulotome according to the invention, a hole in the extension of the valvulotome close to the attachment point of the blade directs a jet or a spray of solution in the direction of the blade. The spray of solution impinges on the inside surface of the second leaflet and the pressure of the solution inflates the edge of the second leaflet against the shaft of the valvulotome. This enables the blade to engage the leaflet, the proximal end of the blade to enter and pierce the valve pocket, and the blade to cut the leaflet successfully. Alternatively, the extension can be arranged to direct the solution at the blade. The solution then flows along the blade and into the inside of the second leaflet.

In a further variation of a valvulotome according to the invention, the shaft of the valvulotome is provided with a laterally-offset marker. The laterally-offset marker is a projection from the shaft of the valvulotome on the opposite side of the shaft from the cutting blade. The laterally-offset marker enables the rotational orientation of the valvulotome in the vein to be unambiguously determined by external observation. The laterally-offset marker increases the width of the valvulotome so that it is somewhat larger than the diameter of the vein. When the valvulotome is inserted in the vein, the valvulotome distorts the vein. The resulting imprint of the laterally-offset marker can be seen on the outside wall of the vein and the resulting imprint of the shaft can be seen on the outside wall of the vein substantially opposite to the imprint of the laterally-offset marker. The imprint of the laterally-offset marker appears different from the imprint of the shaft, enabling the rotational orientation of the valvulotome to be determined even if the vein is so opaque as to prevent the color markings of the valvulotome from being observed. In the preferred embodiment, the laterally-offset marker is provided by a U-bend in the shaft, close to its proximal end. The U-bend bends, relative to the shaft, in substantially the same direction as the lateral displacement of the extension.

In a yet further variation of a valvulotome according to the invention, a first convex spring piece is attached to the shaft towards its distal end. A second convex spring piece is attached to the distal end of the extension as a further extension. The convex spring pieces are coplanar with the blade, but are both on the opposite side of the shaft from the blade. The convex spring pieces increase the overall width of the valvulotome so that it is somewhat greater than the diameter of the vein. The convex spring pieces thus keep the tip, the shaft and the blunt edge of the blade in contact with the wall of the vein and make it even easier for the proximal end of the blade to engage a leaflet when the valvulotome is withdrawn from the vein.

BRIEF DESCRIPTION OF THE DRAWINGS

FIG. 1 shows a perspective view of a valvulotome according to the invention attached to a syringe, inserted in a vein, and in position to cut a first leaflet.

FIG. 2 shows an elevational view of a valvulotome according to the invention.

FIG. 3A shows a plan view of the blade of a valvulotome according to the invention.

FIG. 3B shows a cross section of the blade of a valvulotome according to the invention on the line indicated in FIG. 3A.

FIG. 3C shows a cross section of an alternative embodiment of the blade of a valvulotome according to the invention on the line indicated in FIG. 3A. This embodiment has a widened back.

FIG. 4A shows a cross sectional view of part of a valvulotome according to the invention after it has pierced the apex of one leaflet and shows the flow of physiologic solution.

FIG. 4B is an edge view of the head of a valvulotome according to the invention showing the tip, the dull edge of the blade, and the jet hole.

FIG. 6 is a side view of the head of a valvulotome with a spheroidal tip according to the invention. The areas of darker color are shown by shading.

FIG. 7 is a side view of the head of a valvulotome with a flexible tip according to the invention. The areas of darker color are shown by shading.

FIG. 8 is a side view of a valvulotome with a U-bend according to the invention to indicate the rotational orientation of the valvulotome.

FIG. 9 is a side view of a valvulotome equipped with convex spring parts according to the invention.

FIG. 10 is a side view of a valvulotome according to the invention in a vein showing how the shape of the valvulotome prevents it from entering a side branch of the vein.

FIG. 11 is a side view of a prior art Mills valvulotome in a vein showing the tendency of such a valvulotome to enter a side branch of the vein when the prior art valvulotome is correctly oriented to cut a valve leaflet. The figure also shows how the Mills valvulotome places the leaflet in compression while cutting the leaflet.

DETAILED DESCRIPTION OF THE INVENTION

Figure 5A:
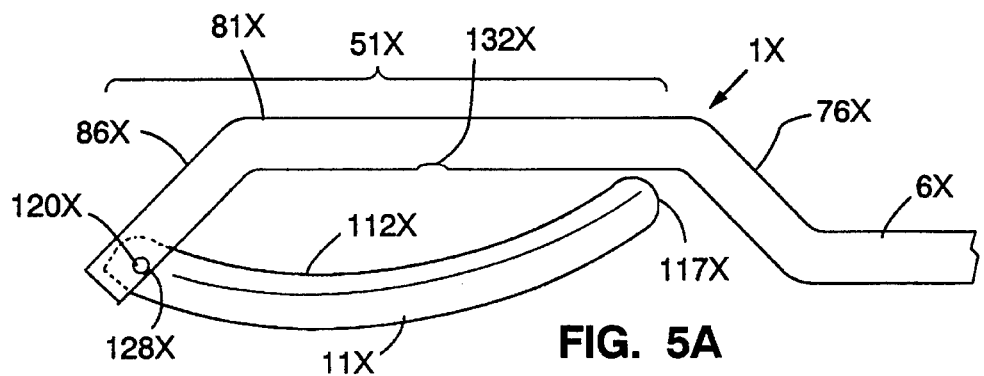
FIG. 5A is a side view of a pivoting blade valvulotome according to the invention. The blade is shown in its closed position.

FIG. 1 shows a valvulotome 1 according to the invention in position in a vein V. The valvulotome 1 is shown with its blade 11 in position in the valve pocket P1, about to pierce the apex of the leaflet L1. The vein V, normally a saphenous vein, but the valvulotome can be used in other veins, includes a valve Va1 comprising two leaflets, a first leaflet L1 and a second leaflet L2. On the distal side of the valve Va1, i.e., closer to the heart, is a side branch B1. More proximal on the vein is a second valve Va2 with a second side branch B2 on its distal side. When the vein is in the leg, blood flows in the vein in the direction indicated by the arrow BF. This will be called the "normal direction."

The valvulotome 1 is shown in detail in FIG. 2. The shaft 6 is preferably made from a piece of no. 19 stainless steel tubing with an outside diameter of about 0.042" (1.1 mm), an internal diameter of 0.027" (0.7 mm), and a length of about 10.5"(265 mm). Making the shaft from stainless steel tubing provides a rigid valvulotome preferable for use in CABG procedures. The shaft 6 may also be made flexible so that the valvulotome can be used in in-situ bypass procedures. In this case, the preferred material for the shaft is ABS tubing (a terpolymer of acrylonitrile, butadiene and styrene) with the same internal diameter as no. 19 stainless steel tubing, and a somewhat larger outside diameter.

A plastic female luer hub 21 is attached with glue to the proximal end of the shaft 6. The extension 51 is laterally displaced from the shaft 6 to provide a recess 46 in which the blade 11 fits such that the blunt back side 102 of the blade is substantially coaxial with the shaft 6.

The extension 51 is preferably formed from the same piece of no. 19 stainless steel tubing as is used for the shaft 6. If an ABS shaft used, a separate stainless steel extension is formed which is then attached to the shaft. In the preferred embodiment, the extension 51 is formed by making three approximately 45 degree bends 61, 66, and 71 in the stainless steel tubing. Between the bends are three substantially straight sections. Between the bends 61 and 66 is a first, short, section 76. Between the bends 66 and 71 is a second, longer, section 81 that is substantially parallel to the shaft 6. Between the bend 71 and the distal end of the extension 51 is a third, short section 86 that is substantially perpendicular to the first section 76. Bends 61 and 66 may merge into one another and, as a result, the first section 76 may lack any discernable straight part. The third bend 71 is made such that the distal end of the section 86 is substantially in line with the longitudinal axis of the shaft 6. In the preferred embodiment, the extension 51 is about 0.7" (18 mm) long and 0.15" (3.8 mm) offset.

The extension 51 may be formed differently from the preferred way just described: for example, it can have a continuous curve instead of three discrete bends. Alternatively, the third bend 71 and third section 86 can be dispensed with and the blade 11 attached to the distal end of the second section 81. In this alternative, the shape of the blade 11 is changed to enable it to be attached to the second section 81 instead of the third section 86, but the distal end of the blade 11 provides substantially the same profile for the distal end of the valvulotome 1 as that shown in FIG. 2.

Details of the blade 11 are shown in FIG. 3A. The blade 11 is preferably made from stainless steel about 0.008" (0.2 mm) thick, and is preferably photo etched to the profile shown in FIG. 3A. The back 102 of the blade is substantially straight over most of its length. The proximal part of the back of the blade indicated by the numeral 107 is curved inwards towards the extension 51. The curved part 107 of the back of the blade is curved towards the extension 51 to reduce the possibility of the proximal end of the blade from snagging the wall of the vein or entering a side branch when the valvulotome is withdrawn. The curved part 107 of the back of the blade is also curved to enable the proximal end 127 of the blade to seat more deeply in the valve pocket when the walls of the vein near the valve are inflated by fluid pressure. The similarity between the curvature of the curved part 107 of the blade and the curvature of the inflated wall of the vein can be seen in FIG. 4A. The back 102 of the blade is radiused and deburred, and hence is blunt, as shown in FIG. 3B, to minimize the possibility of it damaging the vein wall.

Alternatively, the blade could be provided with a back 102A that is substantially thicker (about 0.065"-1.65 mm) than the rest of the blade, as shown in FIG. 3C. This will further reduce the possibility of damaging the vein wall. Additionally, the thicker back 102A is easier to see through the vein wall. The blade could be provided with the thicker back 102A by rolling or bending the back portion of the blade relative to the rest of the blade. Alternatively, the thicker back could be provided by injection molding as part of the bead 157.

The cutting edge 112 of the blade is opposite the back 102 of the blade, is preferably curved as shown in FIG. 3A, and is ground to give it a sharp edge between the extremities indicated by the numerals 117 and 122. The curved shape of the cutting edge 112 enables the cutting edge to cut the valve leaflet effectively while minimizing the possibility of the cutting edge accidentally damaging the vein. The curvature of the cutting edge 112 substantially matches the curvature of the curved part 107 of the back of the blade. This enables the proximal end 127 of the blade to have a relatively large radius instead of a point that would be more likely to damage the vein accidentally. The blade 11 broadens towards its distal end, which enables the cutting edge 112 to cut the leaflet all the way to the edge of the leaflet while maintaining the back 102 of the blade in contact with the wall of the vein.

As already mentioned, the proximal end 127 of the blade 11 is relatively broad and is radiused across its width. Like the back 102 of the blade, the proximal end 127 is deburred and radiused across its thickness and is therefore blunt to minimize the possibility of it accidentally damaging the vein when the valvulotome 1 is withdrawn. The proximal end 127 of the blade pierces the pocket of the valve during the cutting process, but is only able to pierce when working against the relatively high resistance provided by the leaflet (e.g., L1, L2) close to its apex (e.g., P1, P2).

Other parts of the blade 11 are concerned with mounting the blade in the extension 51. The distal end 132 of the blade is cut at about 45 degrees relative to the back 102 of the blade. The angle of the distal end 132 of the blade relative to the back 102 must match the angle between the third section 86 of the extension 51 (FIG. 2) and the shaft 6. This ensures that the back 102 of the blade is substantially parallel to the longitudinal axis of the shaft 6.

The blade 11 is preferably spot welded to one side of the third section 86 of the extension 51 such that the second section 81 of the extension 51 shields the cutting edge 112 of the blade, as shown in FIGS. 4A and 4B. The blade 11 is angled relative to the axis of the shaft 6 so that the proximal end of the blade 127 is in line with the axis of the shaft, as shown in FIG. 4B.

Alternatively, a slot 147 can be formed in the center of the inner face of the distal part of the third section 86, and the distal end of the blade 11 can be spot welded in the slot. This way, the blade is parallel to the axis of the shaft.

The blade 11 is attached to the third section 86 of the extension 51 such that the distal end of the back 102 of the blade is flush with the distal end of the third section 86. The blade 11 is also attached such that the gap between the inner part of the proximal end 127 of the blade and the second section 81 of the extension is preferably about 0.050" (1.2 mm). This distance is small enough to enable the second section 81 to effectively shield the cutting edge 112 of the blade, yet is large enough to admit the thickest part of the leaflet for cutting.

The preferred embodiment of the blade 11 also includes the blade extension 152 on which is mounted the tip 157. The tip 157 provides the valvulotome 1 with a very dull nose. Providing the valvulotome 1 with a very dull nose ensures that the valvulotome 1 has a minimal ability to pierce as it is advanced through the vein, and thus minimizes the possibility of the valvulotome damaging the vein. FIGS. 4A, 4B, and 6 show a substantially spheroidal tip 157 of metal or plastic. The tip 157 is preferably injection molded directly around the blade extension 152. Alternatively, a molded tip 157 can be secured in place by a suitable adhesive, such as an epoxy adhesive, or the tip can be a press fit, secured by the tabs 167.

An alternative to the spheroidal tip 157 is shown in FIG. 7 in which a flexible tip 172 is attached to the blade extension 152. The flexible tip 172 is a hollow cylindrical piece of a flexible silicone plastic and is attached to the blade extension 152 by a suitable adhesive, such as an RTV silicone adhesive, or alternatively is a push fit on the blade extension 152, secured by the tabs 167 (FIG. 3A). The flexible tip 172 is not only very dull like the spheroidal tip 157, but is also soft, which further reduces the possibility of damaging the vein when the valvulotome 1 is advanced.

The blade extension 152 may be dispensed with and a suitable tip be mounted on the end of the third section 86 (FIG. 2). Alternatively, the end of the third section 86 may be suitably flattened and shaped to provide the valvulotome 1 with a dull nose without the need for a separate component.

The blade 11 may optionally include a traction point 181 positioned about half-way across the width of the blade and positioned along the length of the blade such that it is close to the extension 51, as shown in FIG. 3A. The traction point 181 is preferably a hole about 0.03" (0.76 mm) in diameter. A suture attached to the traction point 181 enables the valvulotome 1 to be advanced through the vein by pulling on the suture. The suture applies a tensile force to the valvulotome. Pulling the valvulotome through the vein can be used as an alternative to, or in addition to, pushing the valvulotome through the vein using the column strength of the shaft 6.

The suture attached to the traction point 181 may be attached to a fiber-optic viewing scope. With this arrangement, the scope applies the tensile force to the valvulotome to advance the valvulotome up the vein. The suture maintains a fixed distance between the scope and the blade 11 of the valvulotome, which ensures that the blade remains in the field of view and in the focal plane of the scope.

The dull nose, curved blade, and extension of the valvulotome according to the invention enable the valvulotome to be advanced and withdrawn in the vein with a minimum likelihood of causing damage. The valvulotome presents large, blunt surfaces to the walls of the valvulotome. The effective dimensions of the surfaces that the valvulotome according to the invention presents to the vein, i.e., the tip, the back of the blade, and the extension, are large compared with the diameter of side branches, enabling the valvulotome to resist entering side branches. FIG. 10 shows the valvulotome 1 being withdrawn to cut the valve Va1. The length of the blade 11 is such that the blunt back 102 of the blade spans the mouth of the side branch SB. This prevents the blade from entering the side branch SB and possibly damaging the side branch SB or the vein V in the vicinity of the side branch SB.

The prior art Mills valvulotome M shown in FIG. 11 presents to the vein a surface, namely, the surface of the tip T, the effective dimensions of which are comparable with the diameter of mouth of the side branch SB. This enables the tip T accidentally to enter the mouth of the side branch SB relatively easily. The tip T entering the mouth of the side branch SB exposes the junction of the side branch SB and the vein V to the sharp cutting edge X of the Mills valvulotome. If the surgeon withdraws the valvulotome with its tip T engaged in the side branch, the valvulotome will cut down the wall of the vein V and render the vein unusable.

The arrangements for providing irrigation and inflation are shown in FIGS. 1, 4A, and 4B. The purpose of inflating the vein is to enable the location of the valves in the vein to be determined. Additionally, inflation closes the valve tightly around the shaft of the valvulotome 1, and retracts the valve away from the vein wall, improving the access of the proximal end 127 of the blade to the valve pocket P1.

In FIG. 1, the proximal end of the shaft 6 is attached to the plastic luer hub 21, onto which is screwed a standard 5 ml plastic syringe 26. The syringe 26 holds a supply of physiologic solution 31, or some other suitable fluid, and provides a means for pumping the solution 31 up to the valvulotome 1 for inflating the vein and displacing the leaflets L1 and L2. In an alternative embodiment, the length of the shaft 6 of the valvulotome is reduced to about 2.5" (65 mm), and the effective length of the valvulotome 1 is restored by attaching it to the distal end of a hollow stainless steel rod about 12" (305 mm) long. A luer hub, to which a syringe can be attached, is a push fit on the proximal end of the rod.

The valvulotome 1 can emit the physiologic solution 31 in a number of different ways. For instance, FIG. 4A shows a bore 174 in the third section 86 through which the solution is emitted in a forward direction, as indicated by the arrow 177. Alternatively, and preferably, valvulotome 1 can emit the solution 31 in a retrograde direction in a number of different ways. Emitting solution in a retrograde direction is preferable because it directs the solution towards the leaflet being cut. FIG. 4A shows a number of retrograde emission alternatives. A practical embodiment emits solution in only one or two ways. If the valvulotome 1 is not to emit solution in the forward direction, the distal end of the third section of the extension must be sealed. The tip 157 or 172 can be adapted to provide suitable sealing.

A slot 147 (FIG. 4B) can formed in the third section 86 of the extension 51, adjacent to the blade. Solution emitted from the extension 51 through the slot 147 remains in contact with the blade 11, runs down the blade in a laminar flow, as indicated by the arrow 187 (FIG. 4A), and falls off the end of the blade into the valve pocket. Alternatively or additionally, a hole 192, about 0.026" (0.66 mm) in diameter, is drilled in the wall of the third section 86 between the bend 66 and the root of the blade 11. Depending on the geometry of the hole 192, the hole 192 emits solution towards the proximal end 127 of the blade, in a jet or in a fan-shaped spray, as indicated by the arrow 196.

The direction in which the valvulotome emits solution is relatively unimportant when the solution is providing inflation prior to cutting the first leaflet L1. However, cutting the first leaflet L1 releases some pressure. The pressure may drop slowly enough for the valvulotome 1 to be advanced, rotated through 180 degrees and engaged with the second leaflet while there is still sufficient pressure to hold the leaflet L2 against the shaft of the valvulotome 1. Since the purpose of cutting the leaflet L1 is to prevent it holding pressure, sufficient pressure to hold the second leaflet L2 in place cannot be relied upon. If the pressure drops quickly, or if re-positioning the valvulotome is delayed, emitting solution towards the proximal end 127 of the blade enables the solution to impinge on the inner surface of the second leaflet L2 and to enter the valve pocket between the leaflet L2 and the vein wall. The force of the solution presses the leaflet L2 against the shaft of the valvulotome, and enables the blade to enter the valve pocket P2 to cut the second leaflet L2.

Figure 5B:
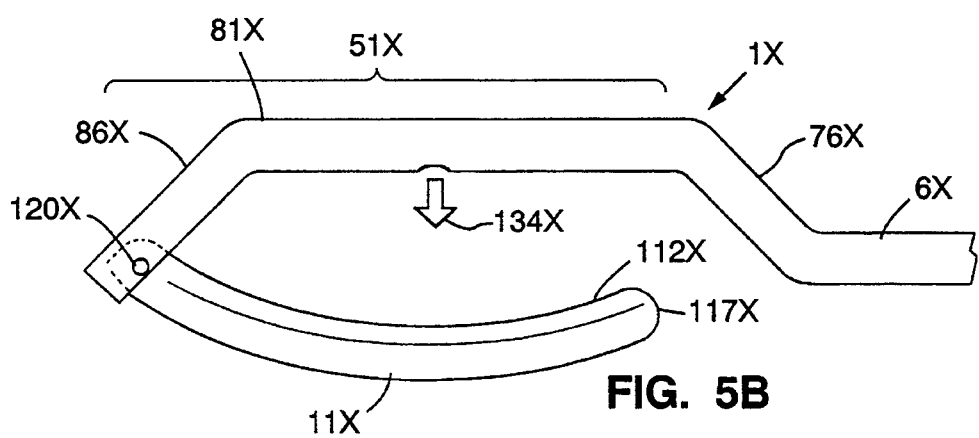
FIG. 5B is a side view of a pivoting blade valvulotome according to the invention. The blade is shown in its open position.

FIGS. 5A through 5E show several embodiments of a pivoting blade valvulotome according to the invention, in which the blade is pivotally mounted in the extension. The pivoting blade valvulotomes further reduce the risk of accidentally injuring the vein, as shown in FIGS. 5A and 5B.

FIG. 5A shows a pivoting blade valvulotome with its blade 11X in the closed position. In this, the cutting edge is moved closer to the extension 51X than in the fixed blade valvulotome shown in FIG. 2. This enables the extension to provide an even greater amount of protection against the cutting edge of the blade accidentally cutting the vein. The lower profile of the pivoting blade valvulotomes allows them to be used in smaller veins.

FIG. 5A shows the proximal end 117X of the blade 11X substantially contacting the second section 81X. The degree of protection provided by the second section may be further increased by providing a slot in the second section to accommodate the blade when the blade is in the closed position.

FIG. 5B shows a pivoting blade valvulotome with its blade 11X swung out into the open position, just prior to cutting a leaflet. With the blade 11X in its open position, a greater clearance can be provided between the proximal end 117X of the blade and the second part 81X of the extension than in the fixed-blade valvulotome shown in FIG. 2. This makes it easier for the proximal end of the blade to enter the valve pocket.

Although the embodiments of the pivoting blade valvulotome differ in detail, they all have closed and open positions corresponding to the closed and open positions shown in FIG. 5A and 5B, respectively.

Figure 5C:
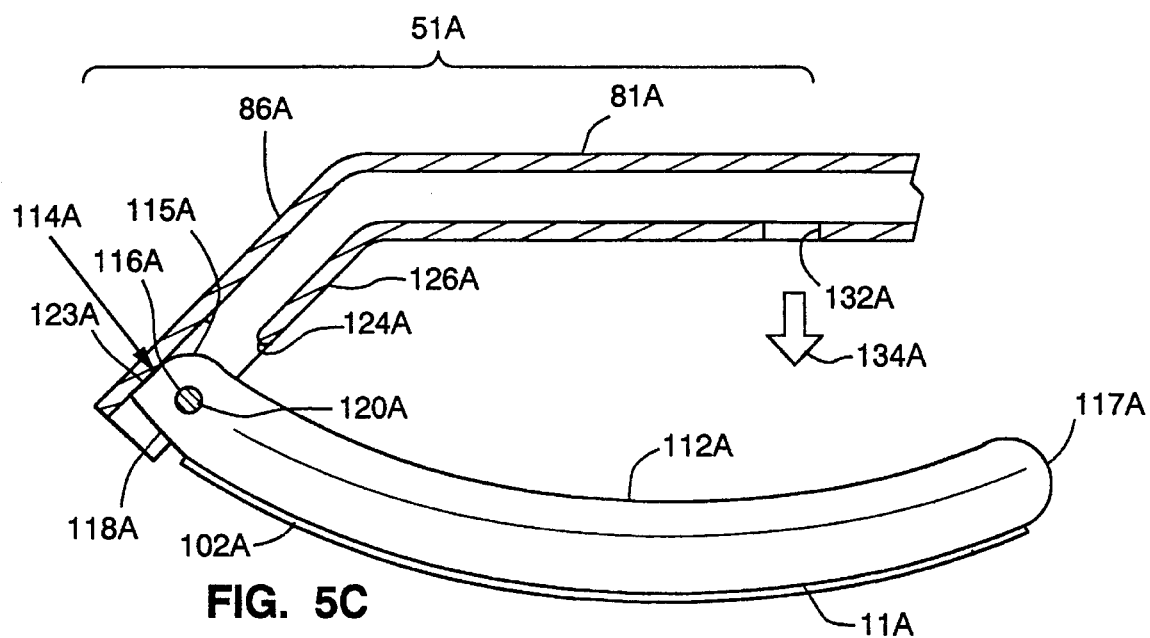
FIG. 5C is an axial cross section of the preferred embodiment of a pivoting blade valvulotome according to the invention. Details of the pivoting of the blade are shown.

The preferred embodiment of a pivoting blade valvulotome according to the invention is shown in FIG. 5C. The blade 11A is similar to the blade 11 shown in FIG. 3A, except that its width is maintained substantially constant along its length, as shown in FIG. 5C. The back 102A of the blade is preferably widened, as shown in FIG. 3C.

The distal end 114A of the blade is shaped with a section 115A, which is quarter-radiused about the pivot hole 116A, and a straight section 123A. The quarter-radiused section 115A allows the blade 11A to pivot in the extension 51A until the straight section 123A juxtaposes the third section 86A. This provides a mechanical limit to the outward movement of the blade 11A in its open position.

The extension 51A is substantially similar to the extension 51 of FIG. 2, but the third section 86A is modified to accommodate the pivoting blade 11A. A slot 124A is cut in the inside face 126A of the distal-most part of the third section. The slot is wide enough to accommodate the blade 11A, and long enough to accommodate the distal portion of the blade 11A when the blade is in its closed position. The slot 124A may be extended proximally into the second section 81A of the extension 51A to accommodate all of the blade 11A, and to reduce further the risk of the cutting edge 112A of the blade 11A accidentally cutting the valve.

The pivot pin hole, similar to the pivot pin hole 128X shown in FIG. 5A, is drilled through the third section 86A, is perpendicular to the slot 124A, and accommodates the pivot pin 120A, which also passes through the pivot pin hole 116A in the blade 11A.

The valvulotome is provided with a jet hole 132A for emitting a jet of solution (indicated by the arrow 134A) towards the blade 11A. The jet of solution impinges on the blade, preferably on the widened back thereof. Additional holes (not shown) may provide a flow of solution down the blade 11A.

In the preferred embodiment, the blade 11A is unbiased. The blade is moved to its closed position by hand before the valvulotome is inserted into the vein. Pressure between the vein wall and the back of the blade maintains the blade in its closed position as the valvulotome is advance through the vein.

When the valvulotome is in position to cut a valve, the blade 11A is moved to its open position by a jet of solution 134A emitted by the jet hole 132A impinging on the blade, preferably on the widened back 102A thereof. Once the blade has been moved to its open position, engaging the proximal end 117A of the blade with the valve leaflet holds the blade in its open position, and the flow of solution may be discontinued if desired.

The blade may be returned to its closed position while in the vein by external pressure exerted through the vein wall by, for example, the surgeon's finger.

Figure 5D:
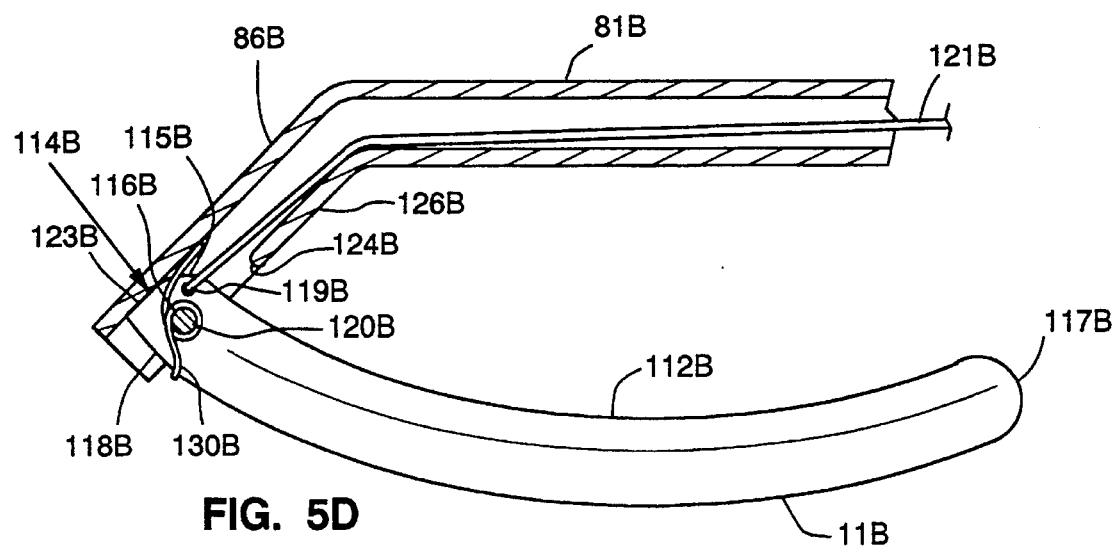
FIG. 5D is an axial cross section of a first alternative embodiment of a pivoting blade valvulotome according to the invention. Details of the pivoting of the blade and the cable operating mechanism are shown.

A first alternative embodiment of the pivoting blade valvulotome is shown in FIG. 5D. In this, the blade 11B is biassed into its closed position by the hairspring 130B, and is pulled towards its open position by the operating cable 121B.

The blade lib and its mounting in the third section 86B of the extension is substantially similar to the blade 11A and its mounting just described, and so will not be described in detail. Corresponding parts use the same reference numbers with the letter "B" instead of the letter "A".

The pivot pin 120B passes through the hairspring 130B, in addition to passing through the pivot pin hole 116B in the blade 11B, and the pivot pin hole 128B in the third section 86B. Opposite ends of the hairspring 130B contact the blade 11B and the inner wall of the third section 86B to bias the blade 11B into its closed position (FIG. 5A).

The blade 11B additionally includes the operating cable hole 119B to which the operating cable 121B is attached. The operating cable runs proximally from the blade 11B through the bore of the shaft 6B, and emerges from the shaft through a fluid-tight seal (not shown) near the proximal end of the shaft. The operating cable is preferably a stainless steel wire, about 0.008" (0.2 mm) in diameter. The operating cable may alternatively be spot welded to the blade 11B.

In use, the operating cable 121B of the alternative embodiment of the pivoting-blade valvulotome 1B is left slack while the valvulotome is advanced through the vein, as will be described in detail below. The hairspring 130B biases the blade 11B into its closed position shown in FIG. 5A. The proximity of the second section 81B to the cutting edge 112B of the blade ensures that the cutting edge of the blade will not accidentally cut the vein.

When the extension 51B of the valvulotome is positioned just beyond the valve to be cut, as will be described in detail below, the surgeon applies tension to the operating cable 121B to move the blade 11B into its operating position, spaced from the second section 81B. The operating cable is pulled until the straight section 123B of the distal end of the blade 11B abuts the third section 86B, which prevents further opening of the blade and allows the pivoted blade to exert the force necessary to cut the valve. Engaging the proximal end 117B of the blade with the valve leaflet holds the blade 11B in its open position, and tension can be removed from the operating cable 121B. This enables the blade to return automatically to its closed position after a leaflet has been cut. The blade is then re-opened using the operating cable 121B when the valvulotome is in position to cut the next leaflet.

In a variation on the pivoting blade valvulotome just described, the operating cable 121B may be dispensed with, and the blade, which would preferably have the widened back shown in FIG. 3C, may be moved into its open position by the force exerted on it by a jet of physiologic solution emerging from a jet hole in the inner face of the second section. This arrangement is similar to the arrangement shown for the preferred embodiment in FIG. 5C, but uses a hairspring to bias the blade into its closed position. Once the blade has been moved to its open position, engaging the proximal end of the blade with the valve leaflet holds the blade in its open position, and the flow of solution may be discontinued if desired.

Figure 5E:
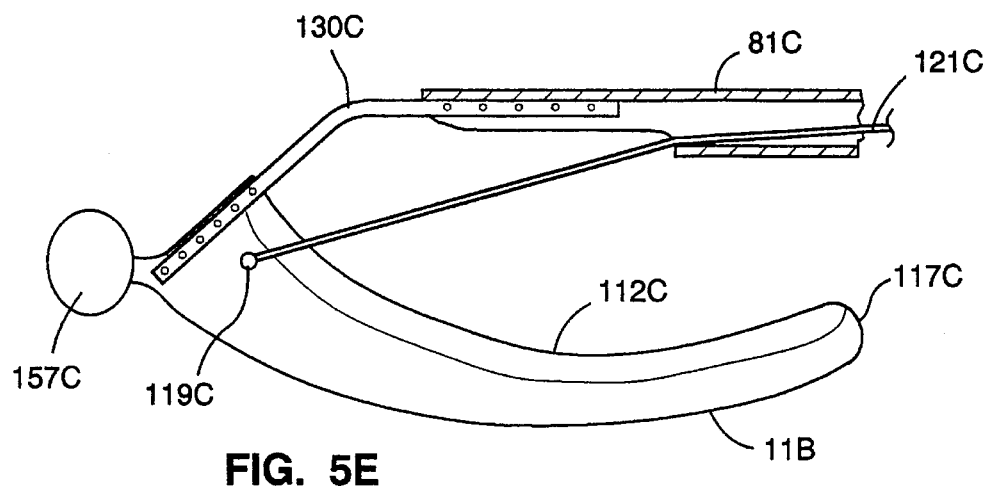
FIG. 5E is a side view of a second alternative embodiment of a pivoting blade valvulotome according to the invention.

A second alternative embodiment 1C of a pivoting blade valvulotome according to the invention is shown is FIG. 5E. In this embodiment, the blade 11C is mounted on a spring-steel blade mount that forms part of the extension. The blade mount enables the blade to move as if it were pivoted between a closed position and an open position corresponding to the closed position and the open position shown in FIGS. 5A and 5B, respectively.

In the preferred embodiment, the spring-steel blade mount 130C is substituted for the third section and part of the second section 81C of the extension 51C. The second section 81C is also shaped as shown to allow the blade carrier 130C to attached to it, preferably by spot welding. The shaping of the second section 81C also provides an optimum operating angle between the operating cable 121C, which emerges from the second section, and the blade 11C.

The blade carrier is preferably a piece of spring steel wire about 0.018" (0.42 mm) in diameter, with a shape similar to that of the third section and the part of the second section of the extension that it replaces.

The blade 11C is shaped substantially the same as the blade 11 shown in FIG. 2, with the addition of the operating cable hole 119A. Alternatively, the operating cable hole can be dispensed with, and the operating cable can be attached to the blade by spot welding. The blade carries the soft tip 157C. The blade is attached to the blade carrier 130C, preferably by spot welding, such that it assumes its open position, as in FIG. 5IC, when no tension is applied to the operating cable 121C.

Applying tension to the operating cable 121C causes the blade carrier 130C to flex, the blade to move to its closed position, as shown for the preferred embodiment in FIG. 5A, with the proximal end 117C of the blade close to the extension 51C, and the extension 5C shielding the cutting edge 112C.

In use, tension is applied to the operating cable 121C of the moving-blade valvulotome 1C to move the blade to its closed position. The valvulotome is then advanced through the vein, as will be described in detail below. The proximity of the second section 81C to the cutting edge 112C of the blade ensures that the cutting edge will not accidentally cut the vein.

When the extension 51C of the moving-blade valvulotome is positioned just beyond the valve to be cut, as will be described in detail below, the surgeon releases the operating cable 121C to move the blade 11C into its open position, spaced from the second section 81C. The valvulotome is then used normally, as will be described below, to cut the first leaflet of the valve. After the first leaflet has been cut, tension may be applied to the operating cable 121C again to return the blade to its closed position before the valvulotome is advanced up the vein to cut the second leaflet. When the valvulotome is in position to cut the second leaflet, tension is released from the operating cable to return the blade to its open position to cut the second leaflet.

FIGS. 6, 7, and 8 show some of the ways in which the valvulotome according to the invention can be adapted to enable its rotational orientation and position in the vein to be observed from outside the vein. FIGS. 6 and 7 show differential coloring, in which the extension 51 and the side of the tip 157 or 172 remote from the blade 11 are colored with a dark color. The dark color, which is shown by stippling 200 in FIGS. 6 and 7, contrasts with the shiny gold color of the blade 11. The contrast can be increased by coloring the tip 157 or 172 in a bright light color 205 on the side opposite to the dark-colored side. Preferred colors are black for the dark color and yellow for the light color. When the valvulotome is in the vein, the rotational orientation of the valvulotome can be determined by bringing the valvulotome into contact with the vein wall and observing the color through the vein wall. The difference between a yellow or gold part of the valvulotome and a black part of the valvulotome can be seen through the translucent wall of the vein.

FIG. 8 shows a variation on the valvulotome 1 for use in veins that are insufficiently translucent for the color orientation indicators just described to be observed. The shaft 6 is provided with a laterally-offset marker in the side of the shaft opposite to the blade 11. In the preferred embodiment of the invention, the laterally-offset marker is provided by the U-bend 210 in the shaft 6. The U-bend 210 is made by making four bends in the shaft 6. The parts of the shaft 6 on opposite sides of the U-bend 210 should lie on the same longitudinal axis. The U-bend 210 is coplanar with the extension 51 and the blade 11, and lies on the same side of the shaft 6 as the extension 51. The depth d of the U-bend 210 is sightly larger than the diameter of the vein in which the valvulotome 1 is to be used. When the valvulotome 1 is inserted into the vein, the U-bend 210 causes the vein to flatten. The imprint of the U-bend 210 can be seen on the outside of the wall of the vein on one side of the vein and the imprint of the shaft 6 can be see on the outside of the wall of the vein on the opposite side of the vein. This unambiguously indicates the rotational orientation of the valvulotome: the cutting edge 112 of the blade faces the same side of the vein as the side on which the imprint of the U-bend 210 can be seen.

A further indication of the orientation of the valvulotome is provided by using an asymmetrical luer lock 21 (FIG. 1). The luer lock 21 can be provided with a flat 23. The luer lock is attached to the shaft 6 so that the flat 23 has a predetermined orientation relative to the blade 11. The preferred orientation of the flat 23 is perpendicular to the blade 11, and on the same side of the shaft 6 as the blade. The asymmetrical luer lock enables the surgeon to determine the orientation of the valvulotome in the vein by feeling the orientation of the flat 23 with his/her thumb or finger, or by observing the orientation of the flat 23.

FIG. 9 shows a variation on the valvulotome 301 that has a greater ability to self-locate in the vein. The valvulotome 301 is similar to the valvulotome 1 previously described except for the addition of two convex spring pieces. Like components are indicated by like numbers with 300 added. The first convex spring piece 303 is attached to the shaft 306. The second convex spring piece 308 is attached to the distal end of the third section 386 of the extension 351, extending out beyond the tip 357. The second convex spring piece 308 has a rounded nose 313 to prevent the spring piece from damaging the vein into which it is inserted. Both convex spring pieces are coplanar with the plane of the extension 351 and the blade 311 but are on the opposite side of the shaft 306 from the blade 311. The convex spring pieces 303 and 308 are preferably made from springy stainless steel and are spot welded to the shaft 306 and the third section 386. Alternatively springy plastic spring pieces 303 and 308 can be attached by means of a suitable adhesive.

The convex spring pieces 303 and 308 increase the overall width of the valvulotome 301 so that it is somewhat greater than the diameter of the vein into which the valvulotome 301 is to be inserted. The convex spring pieces 303 and 308 keep the tip 357, the shaft 306, and the back 302 of the blade in contact with the wall of the vein. This increases the possibility of the proximal end 327 of the blade entering a valve pocket when the valvulotome is withdrawn through the vein.

The convex spring pieces 303 and 308 can be attached to an operating lever (not shown) controlled from the proximal end of the valvulotome. The operating lever elongates the convex spring pieces, which lowers their profile. After the first leaflet of a valve is cut, the operating lever is operated to lower the profile of the convex spring pieces, which allows the valvulotome to be rotated more easily. After the valvulotome has been rotated, the operating lever is the operated once more to raise the convex spring pieces prior to cutting the second leaflet of the valve.

The method according to the invention of using the preferred embodiment of the valvulotome 1 according to the invention to disrupt vein valves in the course of a coronary artery bypass procedure is illustrated in FIGS. 1 and 12A through 12H. The method can also be adapted for use in an in-situ bypass procedure.

A suitably-sized section of the saphenous vein V is removed from the leg and placed on a side table. The side branches, such as B1 and B2 are preferably tied off before the valvulotome 1 is used. This enables the vein to be inflated to determine the location of the valves. The syringe 26 is filled with physiologic solution 31, or some other suitable fluid, and the syringe 26 is screwed onto the luer hub 21. The resulting valvulotome assembly is shown in FIG. 1.

The surgeon places the vein V on the table, and holds it down with one hand. With the other hand, the surgeon carefully inserts the valvulotome 1 into the smaller-diameter end of the vein and advances the valvulotome 1 up the vein. Alternatively, the surgeon can hold the smaller-diameter end of the vein V with tweezers held in one hand.

By starting at the smaller-diameter end of the vein, the valvulotome is advanced in the normal direction indicated by the arrow 5. The valvulotome 1 therefore passes easily though the valves in the vein, such as the valve Va1 shown in FIG. 12A. The surgeon can monitor the progress of the valvulotome from outside the vein by observing the length of the shaft 6 projecting from the proximal end of the vein V. The position of the valvulotome can also be determined by observing the position of colored markings on the valvulotome 1 through the translucent wall of the vein or the imprint of the valvulotome on the vein wall if the vein wall is opaque.

Possible snagging of the valvulotome 1 on a flap on the intimal surface of the vein V as the valvulotome is advanced through the vein can be avoided by using an alternative method of advancing the valvulotome. The alternative method uses the version of the valvulotome 1 that includes the traction point 181 (FIG. 3A). According to the method, the surgeon holds the vein V using one hand, as described above, and threads a guide wire up the vein from the smaller-diameter end with the other hand. When the distal end of the guide wire reaches the larger-diameter end of the vein, the surgeon attaches one end of a piece of suture to the proximal end of the guide wire and, pulling on the distal end of the guide wire, pulls the suture through to the larger-diameter end of the vein V. The surgeon then attaches the other end of the suture to the traction point 181 of the valvulotome assembly. The surgeon then places the valvulotome assembly and the vein V in a linear arrangement on the table and introduces the distal end of the valvulotome 1 into the smaller-diameter end of the vein. The surgeon holds the smaller-diameter end of the vein V with tweezers held in one hand and gently pulls on the suture to advance the valvulotome assembly through the vein V towards its larger-diameter end.

With either method of advancing the valvulotome through the vein V, when the valvulotome reaches the larger-diameter end of the vein, the surgeon withdraws it slightly. The surgeon then grips the larger-diameter end of the vein V with forceps F held in the hand that formerly was holding the smaller-diameter end of the vein V, as shown in FIG. 1. The forceps F grip the vein so as to seal the larger-diameter end of the vein. The forceps F also can clamp the vein to a towel covering the table on which the vein is placed. This secures the larger-diameter end of the vein to the table and enables the surgeon to remove his/her hand from the forceps F when needed.

Figure 12A:
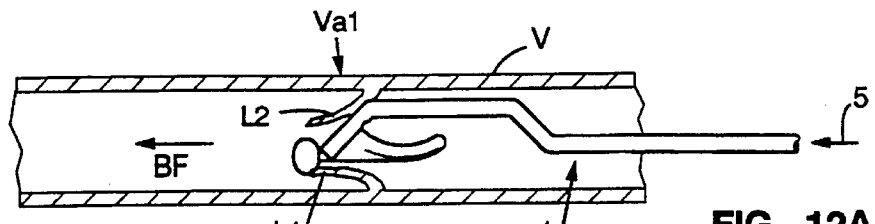
FIG. 12A shows part of a valvulotome according to the invention in a vein being advanced in the blood-flow direction through the vein.
Figure 12B:
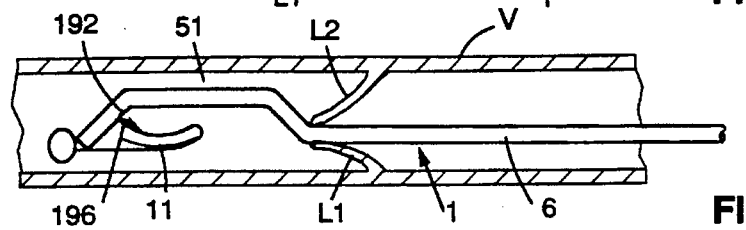
FIG. 12B shows part of a valvulotome according to the invention in a vein after it has been advanced past the most distal valve in the vein. Physiologic solution is emitted from the distal end of the valvulotome to inflate the vein.
Figure 12C:
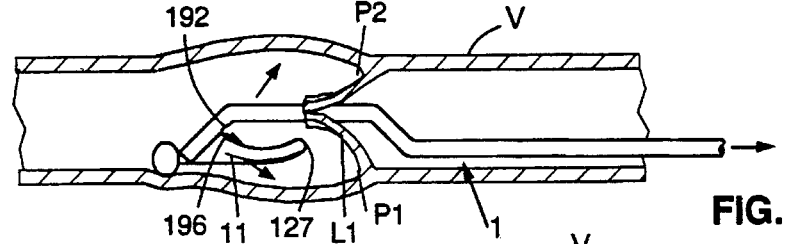
FIG. 12C shows part of a valvulotome according to the invention in a vein. Solution emitted from the valvulotome has inflated the vein to indicate the location of the most distal valve.

The surgeon then depresses the plunger 27 of the syringe 26. This forces physiologic solution out of the syringe 26, through the shaft 6, and out of the hole 192, to form the jet of solution indicated by the arrow 196, as shown in FIG. 12B. The solution entering the part of the vein between the forceps F and the most distal valve Va1 in the vein V creates a pressure differential across the valve Va1 and causes the valve Va1 to close around the shaft 6 of the valvulotome 1. Once the valve Va1 is closed, pressure builds up in the part of the vein between the forceps F and the valve Va1, causing the vein to inflate, as shown in FIG. 12C. The part of the vein below the valve Va1 is not pressurized, and therefore does not inflate. This enables the surgeon to determine the location of the valve Va1 along the length of the vein V. Providing irrigation through the valvulotome enables the valve cutting process to be carried out by a single surgeon without assistance. With conventional techniques, irrigation is introduced into the top of the vein which requires a third hand, i.e., that of an assistant.

Figure 12D:
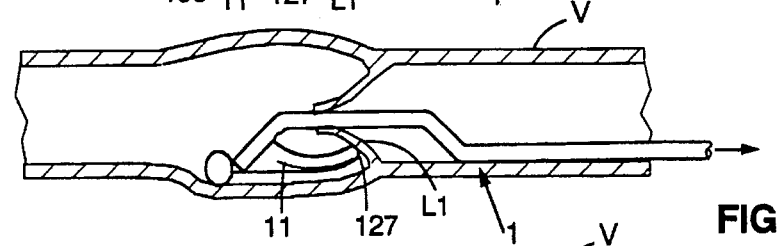
FIG. 12D shows part of a valvulotome according to the invention in a vein. The valvulotome has been withdrawn and the proximal end of its blade has engaged the first leaflet and is sliding up the first leaflet towards the apex of the first leaflet in the base of the valve pocket.

The surgeon observes the position of the extension 51 of the valvulotome 1 in the vein and withdraws the valvulotome 1 until the extension 51 is in the vicinity of the valve Va1. Holding the syringe 26 lightly, the surgeon carefully withdraws the valvulotome 1 until resistance is felt. This indicates that the proximal end 127 of the blade of the valvulotome has contacted one of the leaflets, say the leaflet L1, of the valve Va1. Further gentle withdrawing pressure brings the proximal end 127 of the blade into the valve pocket P1, as shown in FIG. 12D. The surgeon holds the valvulotome gently to allow the valvulotome assembly to rotate as the blade slides up the leaflet L1 to enable the proximal end 127 of the blade to enter into the valve pocket P1 as deeply as possible, and to be centered within the valve pocket.

Figure 12E:
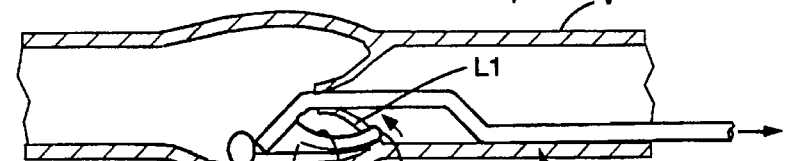
FIG. 12E shows part of a valvulotome according to the invention in a vein. The proximal end of the blade of the valvulotome has pierced the apex of the first leaflet. The curve of the blade fits snugly against the curve of the inflated vein. The arrow indicates the direction of propagation of the cut.
Figure 12F:
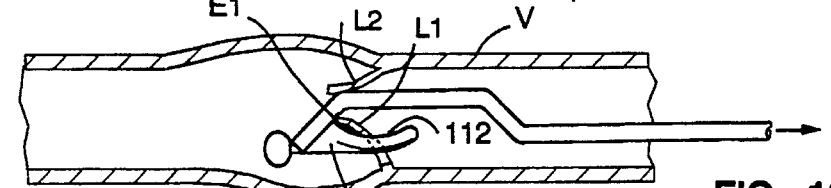
FIG. 12F shows part of a valvulotome according to the invention in a vein. The valvulotome has been further withdrawn and has cut through most of the first leaflet. In cutting the first leaflet, the valvulotome places the leaflet in tension enabling the leaflet easily to provide the resistance necessary for the blade to cut the leaflet cleanly.
Figure 12G:
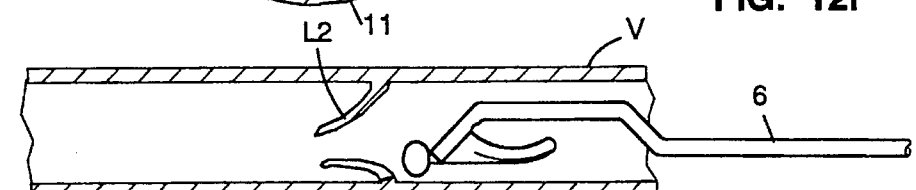
FIG. 12G shows part of a valvulotome according to the invention in a vein. The valvulotome has been further withdrawn and has cut through all of the first leaflet.

With the proximal end 127 of the blade located in the valve pocket, the surgeon applies greater withdrawing pressure to cause the proximal end of the blade to pierce the leaflet L1 at its apex, as shown in FIG. 12E. Once the proximal end of the blade has pierced through the leaflet, the leaflet is exposed to the sharp cutting edge 112 of the blade, which enables the withdrawing pressure to be reduced. The valvulotome assembly is then steadily withdrawn causing the cutting edge 112 of the blade to cut down the center of the leaflet towards the edge E, as shown in FIG. 12F. While cutting, the blade applies a tensile force in the direction away from the apex of the leaflet to the point being cut. The leaflet, being relatively strong in tension, provides the resistance necessary for cutting to take place. Finally, the blade 11 breaks through the edge E1 of the leaflet L1 substantially in the center of the leaflet, as shown in FIG. 12G, and the resistance to withdrawing the valvulotome assembly drops significantly.

The action of the valvulotome according to the invention is to be contrasted with the prior art Mills valvulotome shown in FIG. 11. The Mills valvulotome cuts the leaflet from the edge E towards the valve pocket P1, which places the leaflet in compression, in which direction the leaflet is weak. It is therefore much more difficult to obtain a clean cut up the center of the leaflet from edge of the leaflet to the valve pocket with the Mills valvulotome than to make a clean cut up the center of the leaflet from the valve pocket to the edge with the valvulotome according to the invention.

Figure 12H:
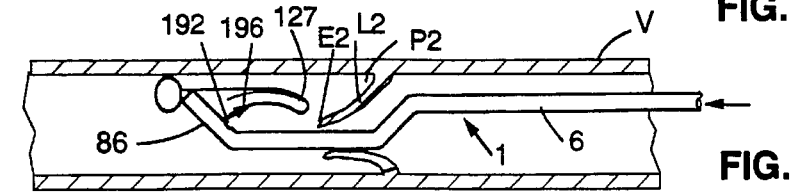
FIG. 12H shows part of a valvulotome according to the invention in a vein. The valvulotome has been axially rotated through 180 degrees and has been advanced back past the valve and is in position to cut the second leaflet of the valve. Solution is emitted from the valvulotome towards the second leaflet to separate the leaflet from the wall of the vein.

The surgeon then advances the valvulotome assembly 1 back up the vein V past the valve Va1. The surgeon can observe the position of the head of the valvulotome through the translucent wall of the vein. Once the blade of the valvulotome has passed the valve Va1, the surgeon rotates the syringe, and hence the valvulotome, through 180 degrees to align the blade with the second leaflet L2, as shown in FIG. 12H. If the cut first leaflet L1 has not allowed much of the solution to pass, and hence the vein above the valve Va1 is still pressurized, the surgeon can proceed with cutting the second leaflet L2 by withdrawing the valvulotome as described above.

In the more likely event that the cut first leaflet L1 has allowed substantially all the solution to pass and the vein above the valve Va1 is unpressurized, the surgeon once more depresses the plunger 27 of the syringe 26 (FIG. 1) to cause solution to be emitted from the hole 192 in the third section 86. A jet of solution indicated by the arrow 196 in FIG. 12H is emitted in the direction of the blade 11 which is aligned with the second leaflet L2. The force of the solution impinging on the leaflet L2 deflects the leaflet L2 away from the wall of the vein and bring it into contact with the shaft 6 of the valvulotome 1.

When the surgeon withdraws the valvulotome assembly, the edge E2 of the leaflet L2 enters the gap between the second portion 81 of the shaft and the proximal end 127 of the blade. Further withdrawal of the valvulotome assembly brings the proximal end 127 of the blade into the valve pocket P2, guided by the inner surface of the leaflet L2. Once the proximal end 127 of the blade has penetrated the valve pocket P2, the leaflet L2 is cut up its center as described above.

After both leaflets L1 and L2 of the valve Va1 have been cut, the surgeon depresses the plunger 27 of the syringe 26 once more to emit more solution into the vein. This pressurizes the part of the vein from the forceps F down to the next valve in the vein, Va2 (FIG. 1), and enables the surgeon to determine the position of the valve Va2. The surgeon cuts both leaflets of the valve Va2 using the procedure described above, and repeats the valve locating and cutting procedure described above until all the valves in the vein have been cut. The vein is then ready for use in a coronary artery bypass procedure.

We claim:

1. A valvulotome, comprising:

an elongate shaft having a distal portion, a cutting blade carried by the distal portion of the shaft, the cutting blade being turned back upon the shaft and including:

a curved cutting edge laterally displaced from, and facing the distal portion of the shaft;

a dull back side opposite the cutting edge; and a proximal end connecting the cutting edge and the dull back side, the proximal end including a dull portion and a portion sharpened to cut towards the shaft;

a distal end, the distal end being an end of the cutting blade adjacent the distal portion of the shaft, the distal end being elongated to extend distally beyond the distal portion of the shaft;

a dull tip carried by the elongated distal end of the cutting blade;

wherein the back side includes a curved part, the curved part extending from part-way along the cutting blade to the proximal end of the cutting blade, and having a curvature curving towards the shaft; and wherein part of the cutting edge is opposite the curved part of the back side, and the part of the cutting edge opposite the curved part of the back side follows the curvature of the curved part of the back side.

2. A valvulotome, comprising:

an elongate shaft having a distal portion, a cutting blade carried by the distal portion of the shaft, the cutting blade being turned back upon the shaft and including:

a curved cutting edge laterally displaced from, and facing the distal portion of the shaft;

a dull back side opposite the cutting edge; and a proximal end connecting the cutting edge and the dull back side, the proximal end including a dull portion and a portion sharpened to cut towards the shaft;

a distal end, the distal end being an end of the cutting blade adjacent the distal portion of the shaft, the distal end being elongated to extend distally beyond the distal portion of the shaft;

a dull tip carried by the elongated distal end of the cutting blade;

wherein the cutting blade includes a proximal part and a distal part, the proximal part including the cutting edge, and wherein the distal part is wider than the proximal part and is attached to the distal portion of the shaft;

wherein the back side of the cutting blade has a curved part, the curved part extending from part-way along the cutting blade to the proximal end of the cutting blade, and having a curvature curving towards the shaft; and wherein part of the cutting edge is opposite the curved part of the back side, and the part of the cutting edge opposite the curved part of the back side follows the curvature of the curved part of the back side.

3. A valvulotome, comprising:

an elongate shaft having a distal portion, a cutting blade carried by the distal portion of the shaft, the cutting blade being turned back upon the shaft and including:

a cutting edge laterally displaced from, and facing the distal portion of the shaft;

a dull back side opposite the cutting edge; and a proximal end connecting the cutting edge and the dull back side, the proximal end including a dull portion and a portion sharpened to cut towards the shaft;

a distal end, the distal end being an end of the cutting blade adjacent the distal portion of the shaft, the distal end being elongated to extend distally beyond the distal portion of the shaft;

a dull tip carried by the elongated distal end of the cutting blade; and wherein at least part of the shaft is substantially different in color from the cutting blade.

4. A valvulotome, comprising:

an elongate shaft having a distal portion, a cutting blade carried by the distal portion of the shaft, the cutting blade being turned back upon the shaft and including:

a cutting edge laterally displaced from, and facing the distal portion of the shaft;

a dull back side opposite the cutting edge; and a proximal end connecting the cutting edge and the dull back side, the proximal end including a dull portion and a portion sharpened to cut towards the shaft;

a distal end, the distal end being an end of the cutting blade adjacent the distal portion of the shaft, the distal end being elongated to extend distally beyond the distal portion of the shaft; and a dull tip carried by the elongated distal end of the cutting blade; and wherein the shaft includes a side facing the cutting blade, opposite a side remote from the cutting blade, and the valvulotome additionally comprises a convex spring piece attached to the shaft on the side remote from the cutting blade.

5. A valvulotome, comprising:

an elongate shaft having a distal portion, an extension extending distally from the distal portion of the shaft and terminating in a dull distal end, a cutting blade, carried by the extension, extending proximally towards the distal portion of the shaft substantially parallel to the shaft and terminating in a proximal end short of the distal portion of the shaft, the proximal end including a dull portion and a portion sharpened to cut towards the extension, the cutting blade including:

a curved cutting edge laterally spaced from and facing the extension; and a dull back side opposite the cutting edge, the back side including a curved part extending from part-way along the cutting blade to the proximal end of the cutting blade, and the curved part having a curvature curving towards the extension; and wherein part of the cutting edge is opposite the curved part of the back side, and the part of the cutting edge opposite the curved part of the back side follows the curvature of the curved part of the back side.

6. A valvulotome, comprising:

an elongate shaft having a distal portion, an extension extending distally from the distal portion of the shaft and terminating in a dull distal end, a cutting blade, carried by the extension, extending proximally towards the distal portion of the shaft substantially parallel to the shaft and terminating in a proximal end short of the distal portion of the shaft, the proximal end including a dull portion and a portion sharpened to cut towards the extension, the cutting blade including:

a cutting edge laterally spaced from and facing the extension; and a dull back side opposite the cutting edge; and wherein at least part of the extension is substantially different in color from the cutting blade.

7. A valvulotome, comprising:

an elongate shaft having a distal portion, an extension extending distally from the distal portion of the shaft and terminating in a dull distal end, a cutting blade, carried by the extension, extending proximally towards the distal portion of the shaft substantially parallel to the shaft and terminating in a proximal end short of the distal portion of the shaft, the proximal end including a dull portion and a portion sharpened to cut towards the extension, the cutting blade including:

a cutting edge laterally spaced from and facing the extension; and a dull back side opposite the cutting edge; and wherein the extension includes a side facing the cutting blade opposite a side remote from the cutting blade, and the valvulotome additionally comprises a convex spring piece attached to the shaft on the side remote from the cutting blade.

8. A method of performing a valvotomy in a vein having a valve comprising a leaflet joined to the vein at a junction, the leaflet having an edge remote from the junction, the method comprising the steps of:

providing a valvulotome comprising an elongate shaft carrying a cutting blade turned back upon the shaft, substantially parallel to the shaft, the cutting blade comprising a cutting edge spaced from and facing the shaft, a dull back side opposite the cutting edge, and a proximal end connecting the cutting edge and the back side, the proximal end including a dull portion and a portion sharpened to cut towards the shaft, moving the cutting blade towards the junction to automatically locate the proximal end of the cutting blade at the junction, piercing the leaflet at the junction using the proximal end of the cutting blade, and applying a tensile force between the cutting blade and the leaflet to cut the leaflet from the junction to the edge.

9. The method of claim 8, wherein:

in the steps of moving the cutting blade towards the junction, piercing the leaflet and applying a tensile force, the shaft is drawn through the vein, and the step of applying a tensile force between the cutting blade and the leaflet causes the cutting edge of the cutting blade to cut the leaflet from where the leaflet was pierced to the edge of the leaflet.

10. The method of claim 8, wherein:

the vein is translucent, in the step of providing a valvulotome a valvulotome is provided having at least part of the shaft substantially different in color from the cutting blade, and the step of moving the cutting blade towards the junction includes determining a rotational orientation of the valvulotome by observing through the translucent vein a contrast between the cutting blade and the differently colored part of the shaft.

* * * * *